US012564432B2

(12) United States Patent
Greiner et al.

(10) Patent No.: US 12,564,432 B2
(45) Date of Patent: Mar. 3, 2026

(54) SURGICAL TENSIONING INSTRUMENT

(71) Applicant: Stryker European Operations Limited, Carrigtwohill (IE)

(72) Inventors: Karl Greiner, Muehlheim (DE); Manfred Schmuck, Muehlheim-Stetten (DE); Daniel Gumpert, Denzlingen (DE); Viktor Kraft, Schallstadt-Mengen (DE)

(73) Assignee: Stryker European Operations Limited, Carrigtwohill (IE)

( * ) Notice: Subject to any disclaimer, the term of this patent is extended or adjusted under 35 U.S.C. 154(b) by 126 days.

(21) Appl. No.: 18/392,980

(22) Filed: Dec. 21, 2023

(65) Prior Publication Data

US 2024/0245439 A1     Jul. 25, 2024

(30) Foreign Application Priority Data

Jan. 25, 2023     (EP) ..................................... 23153286

(51) Int. Cl.
*A61B 17/88* (2006.01)
*A61B 17/00* (2006.01)

(52) U.S. Cl.
CPC *A61B 17/8869* (2013.01); *A61B 2017/00367* (2013.01); *A61B 2017/00831* (2013.01); *A61B 2017/00982* (2013.01)

(58) Field of Classification Search
CPC ............ A61B 17/8869; A61B 17/8861; A61B 17/842; A61B 17/8076
See application file for complete search history.

(56) References Cited

U.S. PATENT DOCUMENTS

| | | |
|---|---|---|
| 3,610,296 A | 10/1971 | Kabel |
| 3,661,187 A | 5/1972 | Caveney et al. |
| 3,712,346 A | 1/1973 | Noorily |

(Continued)

FOREIGN PATENT DOCUMENTS

| | | |
|---|---|---|
| DE | 1300465 B | 7/1969 |
| DE | 1919472 A1 | 10/1970 |

(Continued)

OTHER PUBLICATIONS

Extended European Search Report including Written Opinion for Application No. 23153286.2 dated Jul. 14, 2023, pp. 1-7.

*Primary Examiner* — Amy R Sipp
(74) *Attorney, Agent, or Firm* — Lerner David LLP

(57) ABSTRACT

The present disclosure relates to a surgical tensioning instrument configured to apply a tension to a strap portion of a tensioning member about a target bone or parts thereof. The tensioning member further includes a locking portion configured to cooperate with the strap portion so as to maintain the tension in the tensioning member. The tensioning instrument comprises a clamping mechanism configured to secure the locking portion to the instrument. The clamping mechanism comprises opposed clamping jaws, with at least one of the clamping jaws being configured to be movable between a closed position, in which the locking portion is secured to the instrument, and an open position, in which the locking portion is released from the instrument. The clamping mechanism is specifically operable to move the at least one of the clamping jaws from the closed position to the open position upon its operation.

20 Claims, 13 Drawing Sheets

(56)                    References Cited

U.S. PATENT DOCUMENTS

| | | | |
|---|---|---|---|
| 3,810,499 | A | 5/1974 | Benfer |
| 4,202,384 | A | 5/1980 | Aubert |
| 4,570,340 | A | 2/1986 | Shaw |
| 4,688,607 | A | 8/1987 | Wolcott |
| 4,726,403 | A | 2/1988 | Young et al. |
| 5,057,113 | A | 10/1991 | Mingozzi |
| 5,339,870 | A | 8/1994 | Green et al. |
| 5,417,698 | A | 5/1995 | Green et al. |
| 6,206,053 | B1 | 3/2001 | Hillegonds |
| 7,063,110 | B2 | 6/2006 | Chen |
| 7,806,895 | B2 | 10/2010 | Weier et al. |
| 8,096,998 | B2 | 1/2012 | Cresina |
| 8,096,999 | B2 | 1/2012 | Nesper et al. |
| 8,696,676 | B2 | 4/2014 | Nesper et al. |
| 9,084,644 | B2 | 7/2015 | Knueppel |
| 9,345,465 | B2 | 5/2016 | Aldridge et al. |
| 2004/0059357 | A1 | 3/2004 | Koseki |
| 2008/0262551 | A1* | 10/2008 | Rice .................. A61B 17/8869 606/267 |
| 2015/0038969 | A1 | 2/2015 | Garcia et al. |
| 2015/0305792 | A1 | 10/2015 | Knueppel |
| 2015/0342657 | A1 | 12/2015 | Voisard et al. |
| 2016/0262806 | A1* | 9/2016 | Hsu .................. A61B 17/7053 |

FOREIGN PATENT DOCUMENTS

| | | | |
|---|---|---|---|
| DE | 2214819 | C3 | 12/1973 |
| DE | 2408201 | A1 | 8/1974 |
| DE | 2902560 | A1 | 8/1979 |
| DE | 29612072 | U1 | 9/1996 |
| DE | 10310004 | B3 | 10/2004 |
| DE | 102011008778 | A1 | 7/2012 |
| DE | 102011011778 | A1 | 8/2012 |
| EP | 0299387 | A1 | 1/1989 |
| EP | 597257 | A2 | 5/1994 |
| EP | 0637544 | B1 | 5/1997 |
| EP | 0857466 | B1 | 6/2002 |
| EP | 865334 | B1 | 4/2004 |
| EP | 1400448 | B1 | 10/2005 |
| EP | 1108649 | B1 | 5/2006 |
| EP | 1538083 | B1 | 6/2008 |
| EP | 1599144 | B1 | 7/2010 |
| EP | 2131771 | B1 | 11/2010 |
| EP | 2198791 | B1 | 5/2012 |
| EP | 2670325 | A1 | 12/2013 |
| EP | 1731109 | B1 | 4/2014 |
| EP | 3116424 | A2 | 1/2017 |
| EP | 3137003 | A1 | 3/2017 |
| EP | 2594217 | B1 | 4/2017 |
| EP | 3148462 | B1 | 4/2018 |
| WO | 2012040449 | A1 | 3/2012 |
| WO | 2012106505 | A1 | 8/2012 |
| WO | 2015167920 | A1 | 11/2015 |
| WO | 2016145042 | A1 | 9/2016 |

* cited by examiner

SURGICAL TENSIONING INSTRUMENT

TECHNICAL FIELD

The present disclosure provides a surgical tensioning instrument for a surgical tensioning member to be tensioned about a target bone or parts thereof.

BACKGROUND

In various surgical procedures there is a need to tension a tensioning member about a target bone or parts thereof. Surgical instruments are known which assist a surgeon in reliably and efficiently creating the required tension.

EP 3 116 424 A2 discloses a closure system adapted to secure a first bone portion to a second bone portion. The closure system includes a band, a locking terminal, and a tensioning instrument. The band is adapted to be looped around the first and second bone portions. The locking terminal is adapted to fixedly engage a first portion of the band and selectively fixedly engage a second portion of the band. The tensioning instrument includes a body and a threaded rod. The threaded rod is received in the body and adapted to engage the band such that movement of the threaded rod relative to the body moves the second portion of the band relative to the first portion of the band.

EP 2 670 325 A1 discloses a bone fixation system including at least one bone fixation member and a tensioning instrument. The bone fixation member includes a strap and a locking mechanism. The strap can be pulled through the locking mechanism so as to form a loop about a target bone so as to secure first and second bone segments in an approximated, compressed configuration. The tensioning instrument is configured to apply tension to the loop about the target bone. The tensioning instrument includes a tension assembly that is configured to secure a free end of the bone fixation member to the fixation instrument. The tension assembly is further configured to pull the free end so as to increase tension in the loop while the tension in the loop is less than a select tension.

Currently, surgical tensioning instruments are neither sufficiently easy to handle nor sufficiently reliable.

SUMMARY

Accordingly, there is a need for a surgical tensioning instrument that is easy to handle and reliable.

The present disclosure provides a surgical tensioning instrument configured to apply a tension to a strap portion of a tensioning member about a target bone or parts thereof, with the tensioning member further including a locking portion configured to cooperate with the strap portion so as to maintain the tension in the tensioning member. The tensioning instrument comprises a clamping mechanism configured to secure the locking portion to the instrument, wherein the clamping mechanism comprises opposed clamping jaws, at least one of the clamping jaws being configured to be movable between a closed position, in which the locking portion is secured to the instrument, and an open position, in which the locking portion is released from the instrument. The clamping mechanism is operable to move the at least one of the clamping jaws from the closed position to the open position upon its operation.

The present disclosure further provides a surgical tensioning instrument configured to apply a tension to a surgical tensioning member so as to tension a strap portion of the surgical tensioning member about a target bone or parts thereof, with the surgical tensioning member further including a locking portion configured to cooperate with the strap portion so as to maintain the tension in the surgical tensioning member. The surgical tensioning instrument comprises a body defining a front end and an opposed back end, and a grip movable relative to the body and configured to secure the strap portion of the surgical tensioning member to the surgical tensioning instrument. The instrument further comprises an actuator operatively coupled to the body and configured to move from an initial position toward a tensioning position in response to an applied force, thereby causing the grip to move in a tensioning direction. Further still, the instrument comprises a clamping mechanism configured to secure the locking portion of the surgical tensioning member to the surgical tensioning instrument, wherein the clamping mechanism comprises opposed clamping jaws at the front end of the body, at least one of the clamping jaws being configured to be movable between a closed position, in which the locking portion is secured to the surgical tensioning instrument, and an open position, in which the locking portion is released from the surgical tensioning instrument. The clamping mechanism is operable to move the at least one of the clamping jaws from the closed position to the open position upon its operation.

The at least one movable jaw may be hinged to the body and configured to pivot between the closed position and the open position. The clamping jaws may be symmetrically arranged in the closed position of the clamping mechanism.

The at least one movable jaw may have a central portion between two opposed end portions, and the central portion of the at least one movable jaw may be hinged to the body. The at least one movable jaw may have two opposed ends, a back end closer to the back end of the body and a front end closer to the front end of the body, wherein the front end of the jaw may be hook-shaped. In certain variants, the two clamping jaws may have front ends that are hook-shaped and facing each other. Hook-shaped may, for example, be understood as L-shaped or J-shaped.

The clamping mechanism may comprise a mechanical linkage of components configured to be movable in a direction towards the front end or in a direction towards the back end of the body. The clamping mechanism may be configured to turn a translatory, i.e., linear, movement of one of its components into a rotatory, i.e., pivoting, movement of another one of its components, such as at least one of the jaws.

The at least one movable jaw may be configured to cooperate with (e.g., may be connected to) a rod, which may be operable to move the at least one movable jaw from the closed position to the open position. The rod may only be movable in a translatory manner. The rod may be configured to cause a rotatory movement of the at least one movable jaw.

The rod may be configured to act as a push rod. A pushing movement of the rod may cause the at least one movable jaw to open. The pushing movement may be directed towards the front end of the body.

The rod may form part of the mechanical linkage. The mechanical linkage may comprise at least another rod. Two rods of the mechanical linkage may be connected directly to each other. These rods may be pivotably connected to each other via a joint (e.g., defining common hinge axis). Both rods may each extend along different longitudinal directions. Their longitudinal directions may be at an angle. The angle may be an obtuse angle.

The rod may at least partially extend through the body. The rod may be guided inside the body. The body may allow only a translatory movement of the rod. The rod may be surrounded by the body. The rod may be completely hidden within the body.

The clamping mechanism may comprise a release button protruding from the body and configured to move at least one of the clamping jaws from the closed position to the open position. The release button may comprise a button through-hole, which may extend laterally through the button. The button through-hole may be oblong with a button through-hole back end that is closer to the back end of the body and a button through-hole front end that is closer to the front end of the body.

The button may be movable only linearly. The movement of the button may be limited in both directions, i.e., towards the front end of the body and towards the back end of the body, by means of a button guide, which may be at least one of rod-shaped, fixedly attached to the body and extending through the button through-hole.

A portion of the button may always remain hidden in the body. A button spring may be located between the body and the button, and may bias the button into its initial position. In the initial position, the button may protrude (e.g., as far as possible) from the back end of the body, when the button is not being pushed into the body. In the initial position, button through-hole front end of the button through-hole may contact the button guide. In a completely pushed position, the button through-hole back end of the button through-hole may contact the button guide.

The release button may be configured to actuate the rod. In particular, the button may be configured to push the rod towards the front end of the body and may, in some variants, be configured to pull the rod towards the back end of the body. The button may be directly connected to the rod. The button may be pivotably hinged to the rod. The button and the rod may be inserted into the body and their movement may be limited by the body to a translatory movement. The button and the rod may extend along different longitudinal directions. Their longitudinal directions may be at an angle. The angle may be an obtuse angle.

The at least one movable jaw may be pivotably guided in an elongated cut-out of the rod or of a component coupled to the rod. The cut-out may extend in a first plane, wherein the at least one movable jaw may be configured to move in a second plane from the closed position to the open position, and wherein the first plane may be parallel to the second plane.

The elongated cut-out may be curved such that self-opening of the at least one movable jaw from the closed position to the open position is avoided. The elongated cut-out may be straight or otherwise shaped, as long as there is one portion that is closer to the back end of the body and one portion that is closer to the front end of the body, i.e., as long as they have a portion that extends in a front end back end direction of the body.

The jaws may protrude laterally from the body. One of the jaws may be a fixed or stationary jaw. In other variants, all jaws are movable. The at least one movable jaw may protrude laterally from the body only in the open position. The jaws may be laterally within the body in the closed position of the clamping mechanism or in the closed position of the at least one movable jaw.

The clamping mechanism may be configured such that the closed position is held, when the clamping mechanism is not operated. The clamping mechanism may allow a force acting on the at least one movable jaw directly to close the at least one movable jaw but the clamping mechanism may prevent a force acting on the at least one movable jaw directly to open the at least one movable jaw. For that purpose, the elongated cut-out may be arranged such in the closed position of the clamping mechanism that the end of the jaw movably arrange therein is pressed against a lateral wall of the cut-out, i.e., a wall between the front end and the back end of the cut-out. In fact, as long as all or at least a majority, i.e., more than 50%, of the force applied to the jaw directly for opening it is transmitted by pivoting the jaw about the body and exerted against the lateral wall of the cut-out, the direct opening of the jaw by a force acting directly on the free end of the jaw is avoided or made considerably more difficult. So, a force exerted on the at least one movable jaw for the purpose of self-opening causes the at least one movable jaw to push more towards a lateral wall of the elongated cut-out than in the elongation direction of the cut-out.

The release button may be configured to be pushed from an initial position into the body to move the at least one clamping jaw from the closed position to the open position. The button may be configured to return to its initial position upon release of the button to move the at least one clamping jaw from the open position to the closed position.

The clamping mechanism may be configured to actively move the opposed clamping jaws from the closed position to the open position upon its operation. The clamping mechanism may be configured to actively move the opposed clamping jaws from the open position to the closed position upon a lack of its operation.

There may further be provided a surgical tensioning system comprising the surgical tensioning member comprising the locking portion and the strap portion, and further comprising the surgical tensioning instrument. The at least one movable jaw may be configured to engage the locking portion of the surgical tensioning member in the closed position.

The engagement of the locking portion of the surgical tensioning member by the at least one movable jaw and another opposite movable or immovable jaw may cause the body of the surgical tensioning instrument to be fixedly attached to the locking portion of the surgical tensioning member.

The strap portion may be configured to be pulled through the locking portion along a first direction so as to form a loop about a target bone. The locking portion may be configured to prevent the strap portion from moving there through along a second direction opposite the first direction. In some variants, the strap portion defines a free end that may extend out of the locking portion.

The locking portion may include a locking plate and a locking head. The locking plate and locking head may be formed from different materials. The locking plate may be formed from metal and the locking head may be formed from a polymeric material. The locking plate may be configured to be attached to bone (e.g., via bone screws) and the locking head may be configured to engage the strap portion. The at least one movable jaw may be configured to engage the locking plate, or a portion thereof, in the closed position. The at least one movable jaw may be configured to engage the locking head of the locking portion of the surgical tensioning member in the closed position.

The engagement of the locking head or locking plate of the locking portion of the surgical tensioning member by the at least one movable jaw and another opposite movable or immovable jaw may cause the body of the surgical tensioning instrument to be fixedly attached to the locking head or to the locking plate of the locking portion of the surgical tensioning member.

The present disclosure further provides a surgical tensioning instrument configured to apply a tension to a surgical tensioning member so as to tension the surgical tensioning member about a target bone or parts thereof. The surgical tensioning instrument comprises a grip configured to secure a free end of the surgical tensioning member to the surgical tensioning instrument, with the grip being configured to move in a first direction so as to generate or increase tension in the surgical tensioning member. The instrument further comprises an actuator operatively coupled to the grip, the actuator configured to move from an initial position toward a tensioning position in response to an applied force, thereby causing the grip to move in the first direction. Further still, the instrument comprises a tension limiter connected between the actuator and the grip, wherein the tension limiter allows the grip to move in the first direction when the tension in the surgical tensioning member is less than a tension threshold, and prevents the grip from moving in the first direction when the tension in the surgical tensioning member reaches the tension threshold. The tension limiter comprises a tension limiter spring connected between the actuator and the grip, wherein movement of the actuator from the initial position toward the tensioning position causes the tension limiter spring to stretch, and the stretching of the tension limiter spring causes the tension limiter spring to bias the grip to move in the first direction under a biasing force.

The present disclosure further provides a surgical tensioning instrument configured to apply a tension to a surgical tensioning member so as to tension the surgical tensioning member about a target bone or parts thereof. The surgical tensioning instrument comprises a grip configured to secure a free end of the surgical tensioning member to the surgical tensioning instrument, a traveler that is connected to the grip such that the grip is configured to move in a first direction along with the traveler so as to generate or increase tension in the surgical tensioning member, and an actuator operatively coupled to the traveler, the actuator configured to move from an initial position toward a tensioning position in response to an applied force, thereby causing the traveler to move in the first direction. The instrument further comprises a tension limiter connected between the actuator and the traveler, wherein the tension limiter allows the traveler to move in the first direction when the tension in the surgical tensioning member is less than a tension threshold, and prevents the traveler from moving in the first direction when the tension in the surgical tensioning member reaches the tension threshold. The tension limiter comprises a tension limiter spring connected between the actuator and the traveler, wherein movement of the actuator from the initial position toward the tensioning position causes the tension limiter spring to stretch, and the stretching of the tension limiter spring causes the tension limiter spring to bias the traveler to move in the first direction under a biasing force.

When the tension in the surgical tensioning member reaches the tension threshold or exceeds the tension threshold, any further movement of the actuator towards the tensioning position may cause the tension limiter spring to stretch further and the traveler and/or grip to stop its movement in the first direction. In other words, the traveler and/or grip may remain stationary, while the actuator is moved towards the body.

The tension limiter spring may be enclosed by the actuator. The tension limiter spring may be partially or fully enclosed by the actuator. The tension limiter spring may be visible through the actuator. The tension limiter spring may be a helical spring.

The actuator may extend along a second direction and the tension limiter spring may extend in the second direction. Alternatively, the actuator and the tension limiter spring may extend longitudinally in parallel.

The surgical tensioning instrument may further comprise a tension limiter adjustment mechanism configured to provide an adjustability of the tension threshold by adjustment of an initial pre-stretch of the tension limiter spring. The adjustment mechanism may comprise an adjustable threaded connection configured to alter its longitudinal length.

The adjustment mechanism may be configured to adjust a distance between one part of the tension limiter spring, which is closer to the actuator, and another part of the tension limiter spring, which is closer to the grip and/or traveler. The adjustment mechanism may be configured to adjust a distance between one longitudinal end of the tension limiter spring, which is connected to the actuator, and an opposite longitudinal end of the tension limiter spring, which is connected to the grip and/or traveler. The adjustment mechanism may form a connection link between the tension limiter spring and the actuator. The term connection—as in the entire disclosure—may be refer to a direct or indirect (i.e., via another component) connection.

The surgical tensioning instrument may be a forceps type instrument. One shank of the forceps may be formed by a body of the surgical tensioning instrument and another shank of the forceps may be formed by the tensioning mechanism and/or by the actuator.

The grip may define a grip channel for insertion of a portion of the surgical tensioning member. The grip channel may be configured to lead the surgical tensioning member into a space between the actuator and the body of the surgical tensioning instrument. The grip channel may be formed by a space between the grip and the traveler. The grip channel may be formed on a side of the traveler opposite the body and/or the traveler pivot axis.

The traveler may be pivotably hinged to the grip. The grip may be pivotably hinged to the traveler about a grip pivot axis, preferably independently. The actuator may be pivotably hinged to the traveler about the same grip pivot axis but independently from the grip. A grip spring may be connected between the grip and the traveler and may bias the grip in an initial traveler position relative to the traveler. The grip may have one end portion that is hinged to the other end portion of the traveler via the grip pivot axis. The grip spring may extend between a central portion of the grip and a central portion of the traveler, may be connected at one end thereof to the grip via a connecting axis and at the other end thereof to the traveler, and may bias the grip away from the traveler, thereby opening the grip channel between a central protruding grip portion of the grip and the other end of the traveler for insertion of a surgical tensioning member. The traveler may include a stop for the grip, against which the grip may be biased by the grip spring to define a maximum width of the grip channel.

The actuator may have one end portion that is hinged to the grip by means of the connecting axis.

The actuator may be pivotably hinged to the grip. The actuator may be pivotably hinged directly at one end of the grip, for example to the grip pivot axis. The actuator may further be hinged indirectly, for example via the tension limiter spring at the other end of the grip.

The actuator may be pivotable about one axis and the grip may be pivotable about another axis, and both axes may be collinear. The resulting axis may be the grip pivot axis or the traveler pivot axis.

The actuator may pivot together with the grip and the traveler about the traveler pivot axis, when the tension in the surgical tensioning member is less than a tension threshold. When the tension in the surgical tensioning member is at or above the tension threshold, the grip and the traveler remain stationary, while the actuator pivots either about the connecting axis or about the grip pivot axis.

The surgical tensioning instrument may further comprise a body defining a surgical tensioning member contacting front end of the body and an opposed back end of the body. The front end and the back end of the body may define a longitudinal extension of the body.

The grip, the traveler and the actuator may be pivotably hinged to the body and may be configured to pivotably move in the first direction and towards the body. They may be hinged via the traveler and its traveler pivot axis.

The grip may be configured to move towards and away from the traveler to close and open the grip channel, wherein a grip spring may be connected between the grip and the traveler and may bias the grip away from the traveler and the grip channel into an open initial position.

The body may comprise an interface configured to temporary fix a locking portion of the surgical tensioning member to the body. Additionally, or in the alternative, the body may comprise a pulley configured to lead a free end of a strap portion of the surgical tensioning member extending through the locking portion towards the grip and/or grip channel.

There may further be provided a surgical tensioning system comprising the surgical tensioning member including a locking portion and a strap portion, wherein the strap portion may be configured to be pulled through the locking portion along a third direction so as to form a loop about a target bone, and the locking portion may be configured to prevent the strap portion from moving there through along a fourth direction opposite the third direction. The strap portion may define a free end that may extend out the locking portion. The surgical tensioning system further comprises the surgical tensioning instrument, wherein the tension threshold may be below a breaking tension of the surgical tensioning member.

BRIEF DESCRIPTION OF THE DRAWINGS

The foregoing summary, as well as the following detailed description, will be better understood when read in conjunction with the appended drawings. In the drawings:

FIG. 9 is a lateral view in accordance with FIG. 8, wherein an actuator of the surgical tensioning instrument is initially moved clockwise towards a body of the surgical tensioning instrument to grip and, thereby, secure the strap portion to the surgical tensioning instrument;

FIG. 10 is a lateral view in accordance with FIG. 9, wherein the actuator of the surgical tensioning instrument is further moved clockwise towards the body of the surgical tensioning instrument to tension the surgical tensioning member about the two sternum halves, when the tension in the surgical tensioning member is less than a tension threshold;

DETAILED DESCRIPTION

Figure 1:
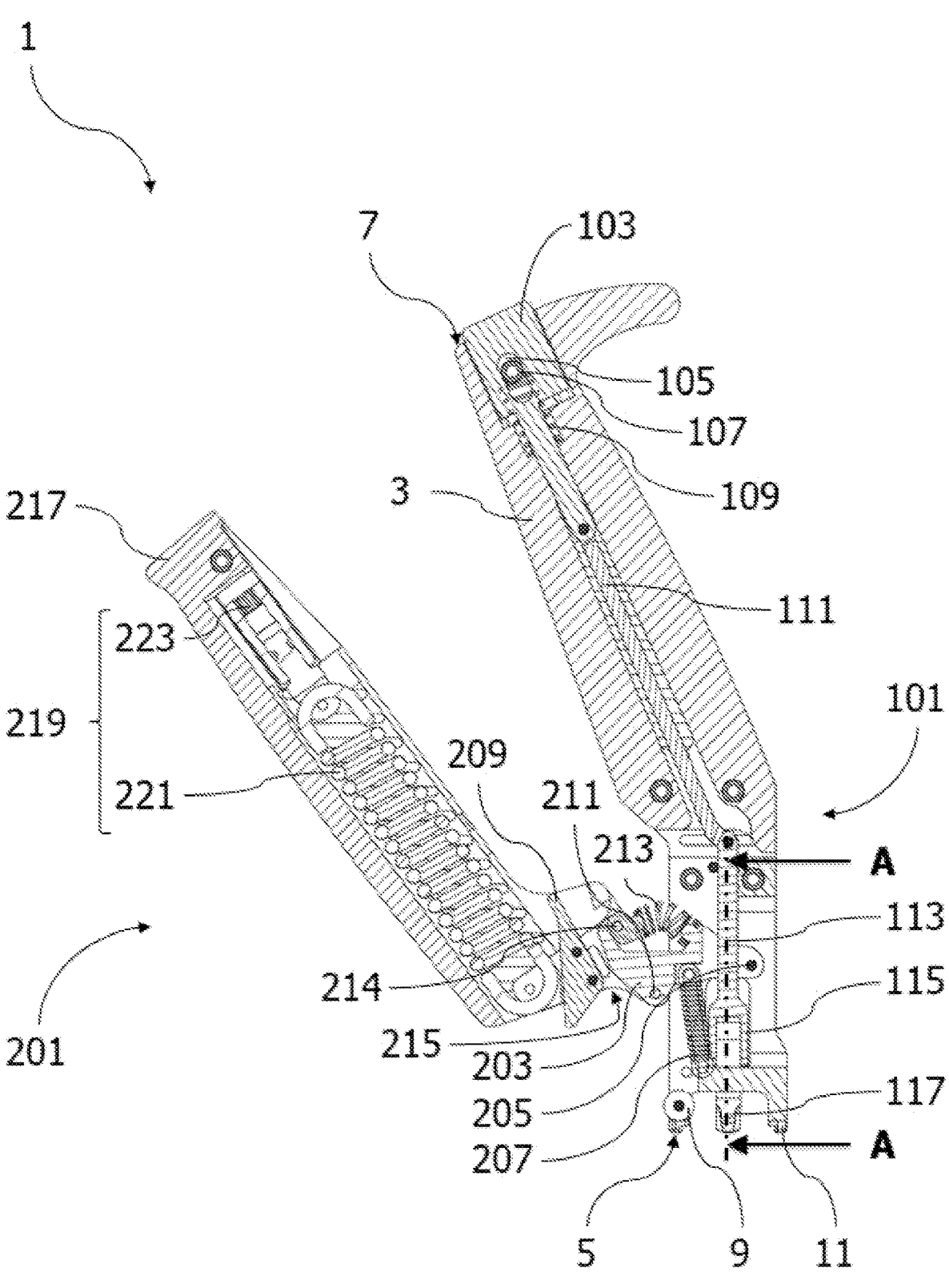
FIG. 1 is a lateral cross-section view of a surgical tensioning instrument with clamping jaws in an open position and a spring member in an initial position.

FIG. 1 illustrates a lateral cross-section view of a surgical tensioning instrument 1, which here is a forceps type instrument.

The surgical tensioning instrument 1 comprises a body 3, which extends longitudinally from a front end 5 to a back end 7. Front end 5 and back end 7 of the body 3 can also be referred to as front portion and back portion of the body 3, thereby not necessarily denoting a certain point but a portion of the body 3.

The body 3 comprises a pulley 9, which is rotatably hinged to the body 3 at the front end 5 thereof. As will be explained in greater detail below, the purpose of the pulley 9 is to guide a surgical tensioning member from the front end 5 towards the back end 7 of the body 3.

The front end 5 of the body 3 comprises an interface 11 configured to temporarily and laterally enclose a locking portion of the surgical tensioning member. Thereby, the locking portion can temporarily be fixed to the body 3, as will also be explained in greater detail below.

Figure 2:
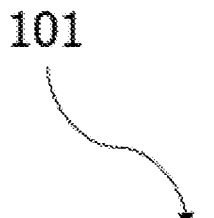
FIG. 2 is a cross-section view of section A-A in FIG. 1 showing the clamping jaws in the open position.
Figure 2:
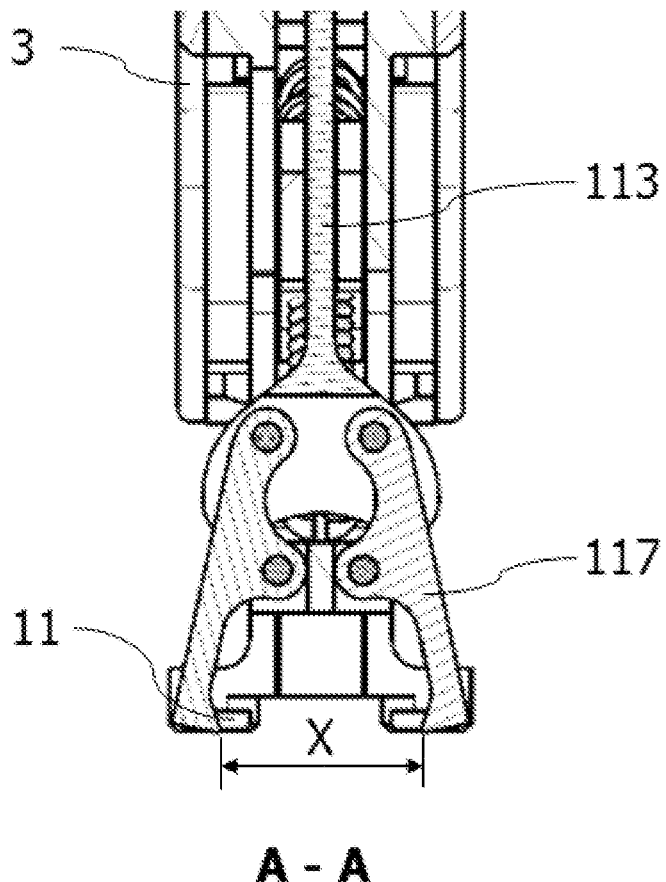
Figure 3:
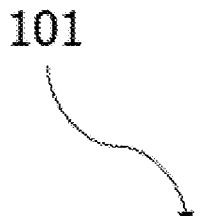
FIG. 3 is a cross-section view in accordance with FIG. 2 showing the clamping jaws in a closed position.
Figure 3:
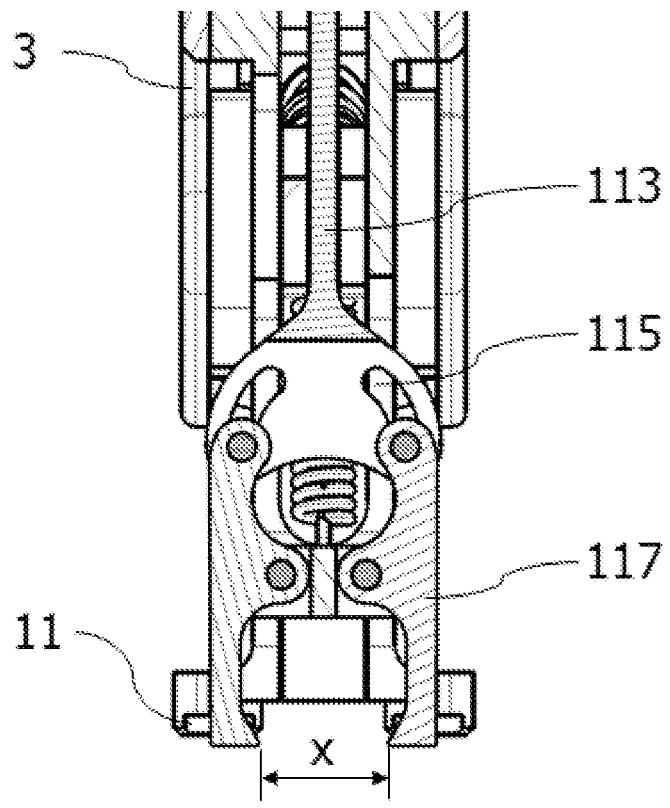

The surgical tensioning instrument 1 further comprises a clamping mechanism 101 and a tensioning mechanism 201, which are both mounted to the body 3. FIG. 2 illustrates a cross-section view of section A-A in FIG. 1 showing an open state of the clamping mechanism 101. FIG. 3 illustrates a cross-section view in accordance with FIG. 2 but showing a closed state of the clamping mechanism 101.

FIGS. 1 to 3 will jointly be referred to in the following to describe the clamping mechanism 101 and the tensioning mechanism 201 of the surgical tensioning instrument 1.
Clamping Mechanism The clamping mechanism 101 of the surgical tensioning instrument 1 illustrated in FIG. 1 comprises a button 103 with a button through-hole 105, a button guide 107, a button spring 109, a first rod 111, a second rod 113 with two second rod through-holes 115, and two clamping jaws 117. The button 103, also referred to as release button herein, comprises the button through-hole 105, which extends laterally through the button 103. The button through-hole 105 is oblong with a button through-hole back end that is closer to the back end 7 of the body 3 and a button through-hole front end that is closer to the front end 5 of the body 3. The button 103 protrudes partially from the back end 7 of the body 3, and is movable only linearly.

The movement of the button 103 is limited in both directions, i.e., towards the front end 5 of the body 3 and towards the back end 7 of the body 3, by means of the button guide 107. The latter is rod-shaped, fixedly attached to the body 3 and extends through the button through-hole 105. Therefore, a portion of the button 103 always remains hidden in the body 3. The button spring 109 is located between the body 3 and the button 103, and biases the button 103 into its initial position. In the initial position, the button 103 protrudes as far as possible from the back end 7 of the body 3, when the button 103 is not being pushed into the body 3. In the initial position, the button through-hole front end of the button through-hole 105 contacts the button guide 107. Here in FIG. 1, the button 103 is in a partially pushed state. In this partially pushed state, the button 103 is in a position, where the button through-hole back end of the button through-hole 105 is closer to the button guide 107 than the button through-hole front end of the button through-hole 105.

With continued reference to FIG. 1, the first rod 111 comprises a back end, which is hinged to the button 103 and extends longitudinally further through the body 3 towards the front end 5 of the body 3. An opposite front end of the first rod 111 is hinged to a back end of the second rod 113, which extends longitudinally even further through the body 3 towards the front end 5 of the body 3. An opposite front end of the second rod 113 comprises symmetrically curved second rod through-holes 115, also referred to as elongated cut-outs, which extend in a common plane. Back ends of the curved second rod through-holes 115 are closer to each other as well as closer to the back end 7 of the body 3 than front ends of the curved second rod through-holes 115, which are further apart from each other. Of course, the second rod through holes 115 may be straight or otherwise shaped, as long as they have one portion that is closer to the back end 7 of the body 3 and one portion that is closer to the front end 5 of the body 3, i.e., as long as they have a portion that extends in a front end 5 to back end 7 direction.

With reference to FIGS. 1, 2 and 3, the clamping jaws 117 extend longitudinally even further through the body 3 and are closest to the front end 5 of the body 3. Back ends of the clamping jaws 117 are pivotably guided in the second rod through-holes 115, their central portions are hinged to the body 3, and their front ends are hook-shaped i.e., L-shaped), and free to be able to secure a surgical tensioning member. Here in FIG. 1, the clamping jaws 117 are in their open position. FIG. 2 shows that open position, where the back ends of the clamping jaws 117 are at the back ends of the curved second rod through-holes 115. FIG. 3 shows the closed position of the clamping jaws 117, where the back ends of the clamping jaws 117 are at the front ends of the curved second rod through-holes 115. FIG. 2 and FIG. 3 also show the symmetrical arrangement of the clamping jaws 117 in both, their open and closed position.

Of course, instead of two, there may be provided just one movable clamping jaw 117 and one corresponding second rod through-hole 115. The other clamping jaw may be immovably fixed to the body 3 and even form part of the interface 11 of the body 3. Moreover, more than two clamping jaws 117 may be provided (e.g., two pairs of opposing clamping jaws).

When the button 103 is pushed, the button 103 is moved from its initial position—protruding as far as possible from the back end 7 of the body 3—further into the body 3 and against the biasing force of the button spring 109. The linear movement of the button 103 is transmitted through the first rod 111 to the second rod 113. The second rod 113 is moved towards the clamping jaws 115 such that the back ends of the clamping jaws 117 are brought closer together at the back ends of the curved second rod through-holes 115 and the front ends of the clamping jaws 117 are spaced further apart to assume their largest distance X from each other, see FIG. 2.

When the button 103 is released, the button spring 109 returns the button 103 to its initial position—protruding as far as possible from the back end 7 of the body 3. The button 103 pulls the first rod 111 and, thereby, the second rod 113 to their initial positions, wherein the second rod 113 pulls away from the clamping jaws 117 and the back ends of the clamping jaws 117 are moved to the front ends of the curved second rod through-holes 115, where they are spaced further apart. This causes the front ends of the clamping jaws 117 to be brought closer together to assume their smallest distance x from each other, see FIG. 3. This initial state, i.e., closed state, of the clamping jaws 117 and of the clamping mechanism 101 is held reliably against an opening force, which may act on the front end of the clamping jaws 117 trying to pivot the clamping jaws 117 around their central portions in order to open the front ends of the clamping jaws 117. Such an opening force on the front end of the clamping jaws 117 causes the back ends of the clamping jaws 117 to push against an inner lateral wall of the second rod through-holes 115 between the front and back ends of the curved second rod through-holes 115, see FIG. 3.
Tensioning Mechanism With reference to FIG. 1, the tensioning mechanism 201 of the surgical tensioning instrument 1 comprises a traveler 203 with a traveler pivot axis 205 and a traveler spring 207, a grip 209 with a grip pivot axis 211, a grip spring 213, a connecting axis 214, a grip channel 215, an actuator 217, and a tension limiter 219 with a stretchable tension limiter spring 221 and a tension limiter adjustment mechanism 223.

The traveler 203 has one end portion that is hinged to the body 3 via the traveler pivot axis 205. The traveler spring 207 extends between a central portion of the traveler 203 and the body 3, and biases the traveler 203 against the body 3.

The grip 209 has one end portion that is hinged to the other end portion of the traveler 203 via a grip pivot axis 211. The grip spring 213 extends between a central portion of the grip 209 and the central portion of the traveler 203, is connected at one end thereof to the grip 209 via the connecting axis 214 and at the other end thereof to the traveler 203, and biases the grip 209 away from the traveler 203, thereby opening the grip channel 215 between a central protruding grip portion of the grip 209 and the other end of the traveler 203 for insertion of a surgical tensioning member. The traveler 203 includes a stop for the grip 209, against which the grip 209 is biased by the grip spring 213 to define a maximum width of the grip channel 215.

The actuator 217 has one end portion that is hinged to the grip 209 by means of the connecting axis 214.

The tension limiter spring 221, here in form of a helical coil spring extending through the actuator 217, has one end portion that is connected to the other end portion of the grip 209. Therefore, the central protruding grip portion of the grip 209 is located between two end portions of the grip 209. The other end portion of the tension limiter spring 221 is connected to the other end portion of the actuator 217 only via the tension limiter adjustment mechanism 223, which is an adjustable threaded connection capable of length adjustment to pre-tension the tension limiter spring 221. Of course, the tension limiter adjustment mechanism 223 can be omitted and the other end portion of the tension limiter spring 221 may be connected directly to the other end portion of the actuator 217. Moreover, other stretchable spring types may be used instead of a coil spring.

In the initial state of the tensioning mechanism 201, the actuator 217 and the body 3 are the furthest apart, and the grip channel 215 is the largest.

Figure 7:
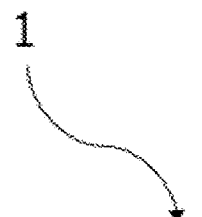
FIG. 7 is a perspective top view in accordance with FIG. 6, wherein the locking portion is in contact with the surgical tensioning instrument, wherein the clamping jaws are in the closed position.
Figure 8:
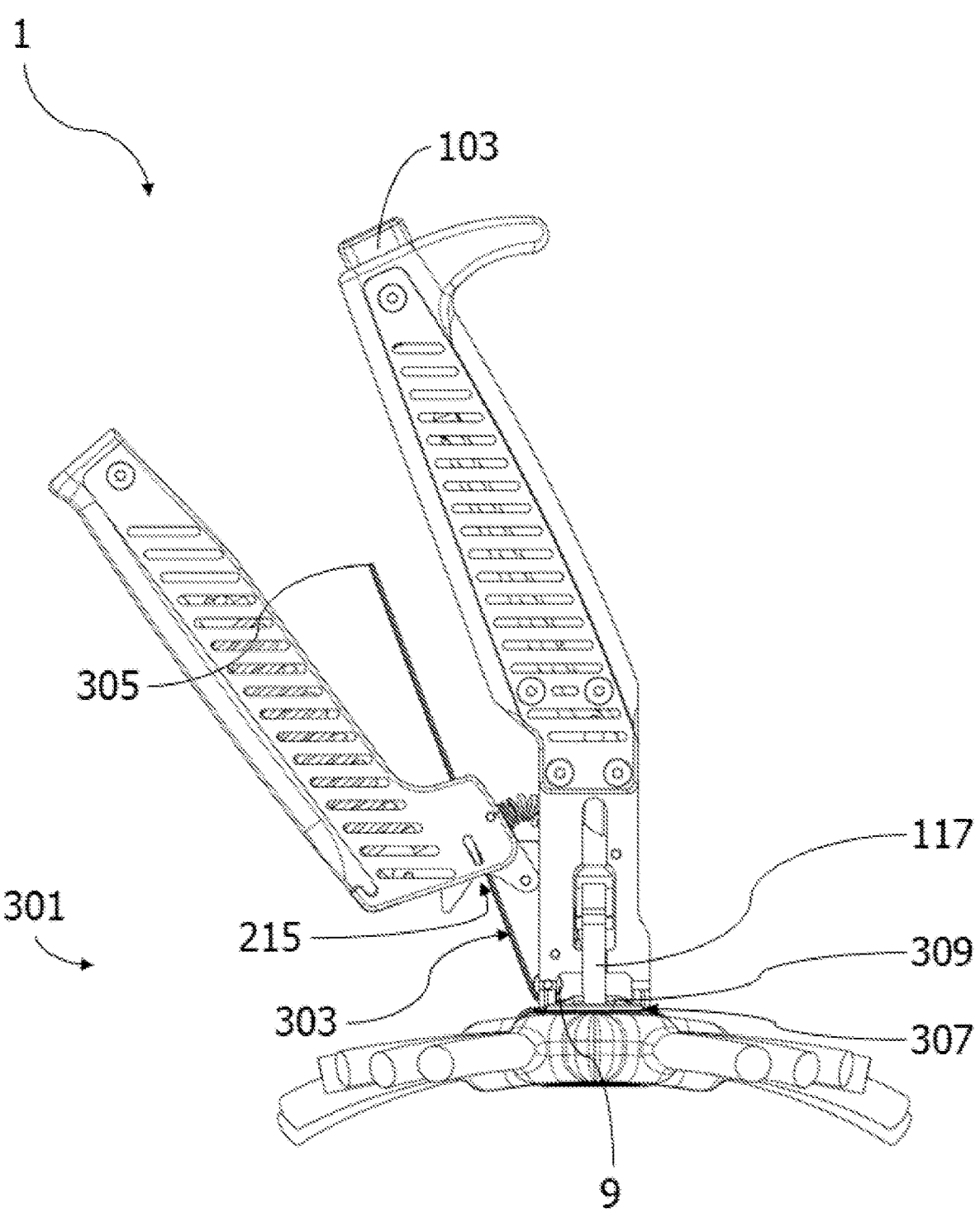
FIG. 8 is a lateral view of the configuration and state shown in FIG. 7.
Figure 9:
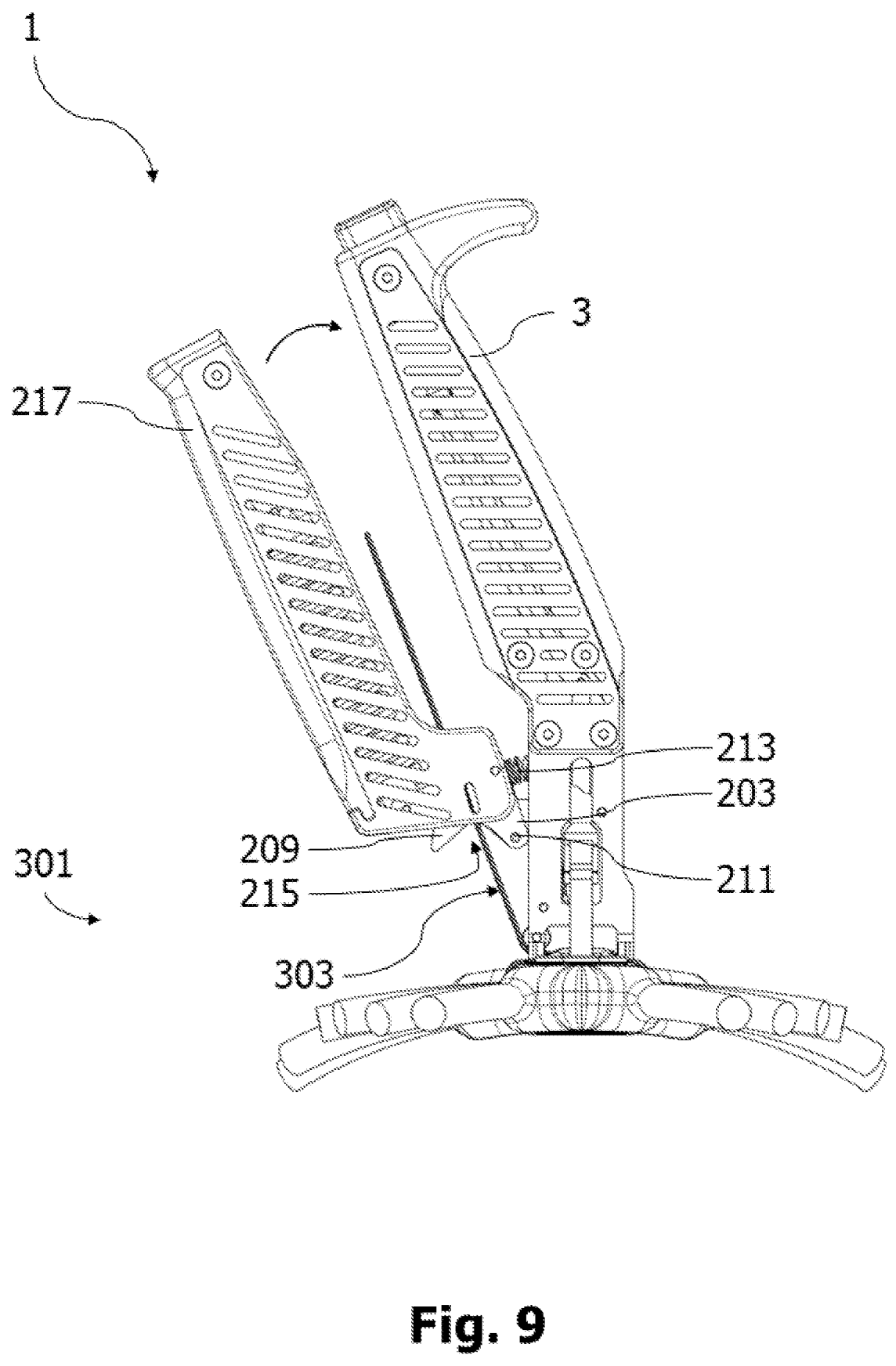

When the actuator 217 is pivoted from its initial state, see FIG. 1, FIG. 7 and FIG. 8, towards the body 3, it first pivots about the grip pivot axis 211 in unison with the grip 209, which causes the grip channel 215 to become smaller and eventually the central protruding grip portion of the grip 209 to abut the traveler 203, either directly by contacting the traveler 203 or indirectly via a surgical tensioning member inserted into and/or through the grip channel 215, see FIG. 9. If a surgical tensioning member is inserted into the grip channel 215, the further movement of the grip 209 depends on whether or not the tension necessary to further tighten the surgical tensioning member is below, or at or above a tension threshold set at the tension limiter 219. Both possibilities shall be described in the following:

Below the tension threshold, the actuator 217 continues pivoting towards the body 3, while continuing pressing the central protruding grip portion of the grip 209 against the traveler 203, but now pivoting the grip 209 and traveler 203 about the traveler pivot axis 205 and against the biasing force of the traveler spring 207. Thereby, the distance between the front end 5 of the body 3 and the grip channel 215 is increased, which causes a further tensioning the surgical tensioning member 301 about the sternum halves, see FIG. 10.

At or above the tension threshold, the actuator 217 continues pivoting towards the body 3, while continuing pressing the central protruding grip portion of the grip 209 against the traveler 203, but now pivoting alone, i.e., only the actuator 217 and the tension limiter 219, about the connecting axis 214 and stretching the tension limiter spring 221. Since the grip 209 and the traveler 203 remain stationary, the distance between the front end 5 of the body 3 and the grip channel 215 is maintained, which causes no further tensioning of a surgical tensioning member gripped in the grip channel 215 and which causes a maintenance of the tension in the surgical tensioning member, see FIG. 11.

As soon as the actuator 217 is no longer actively pivoted towards the body 3 and released, the tension limiter spring 221, the grip spring 213 and the traveler spring 207 return the tensioning mechanism 201 back to its initial state.

FIGS. 4 to 11 will be referred to in the following to describe the process of using the surgical tensioning instrument 1 for a clamping and/or a tensioning.

Figure 12:
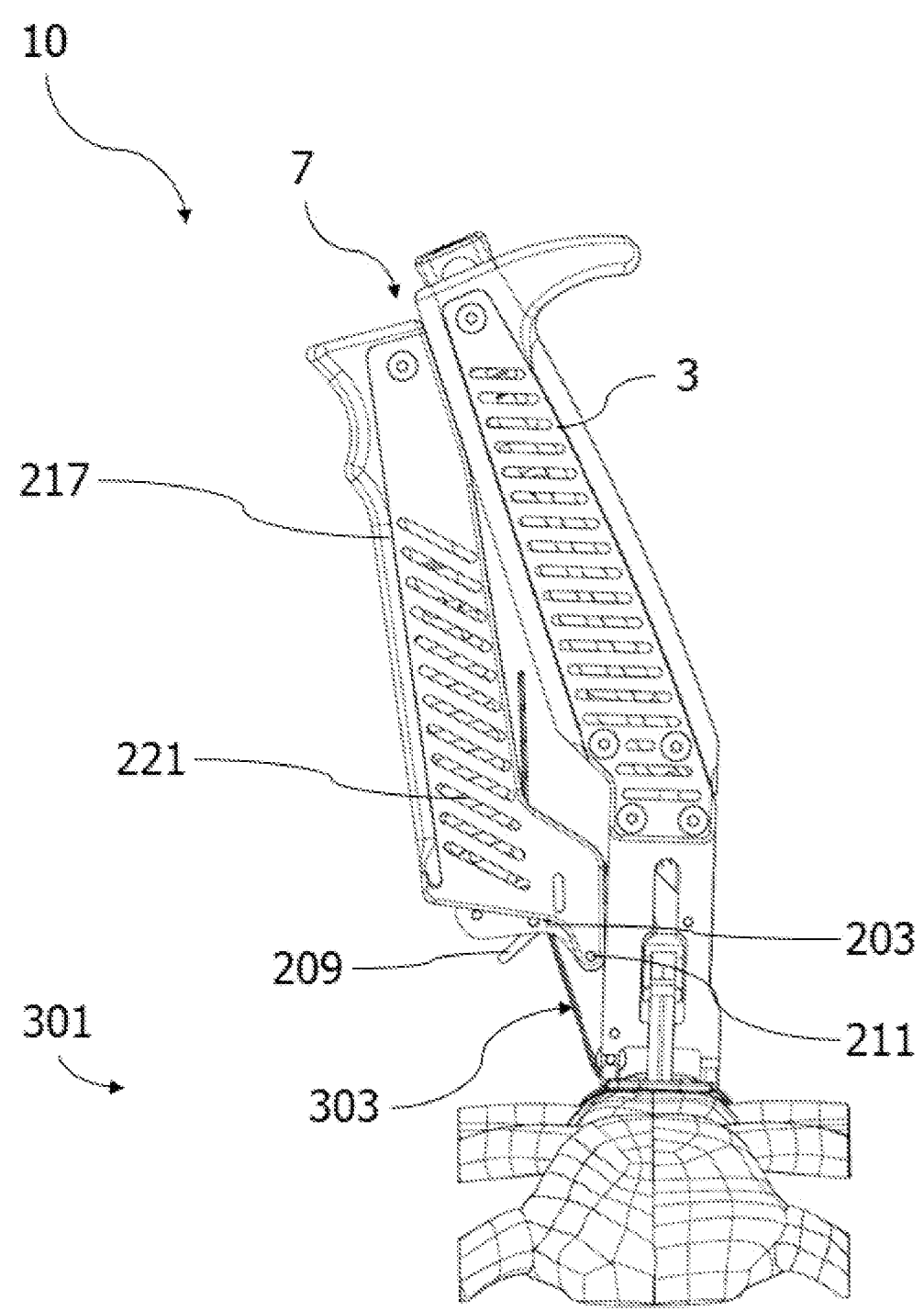
FIG. 12 is a lateral view of an alternative surgical tensioning instrument in the state shown in FIG. 11.
Figure 13:
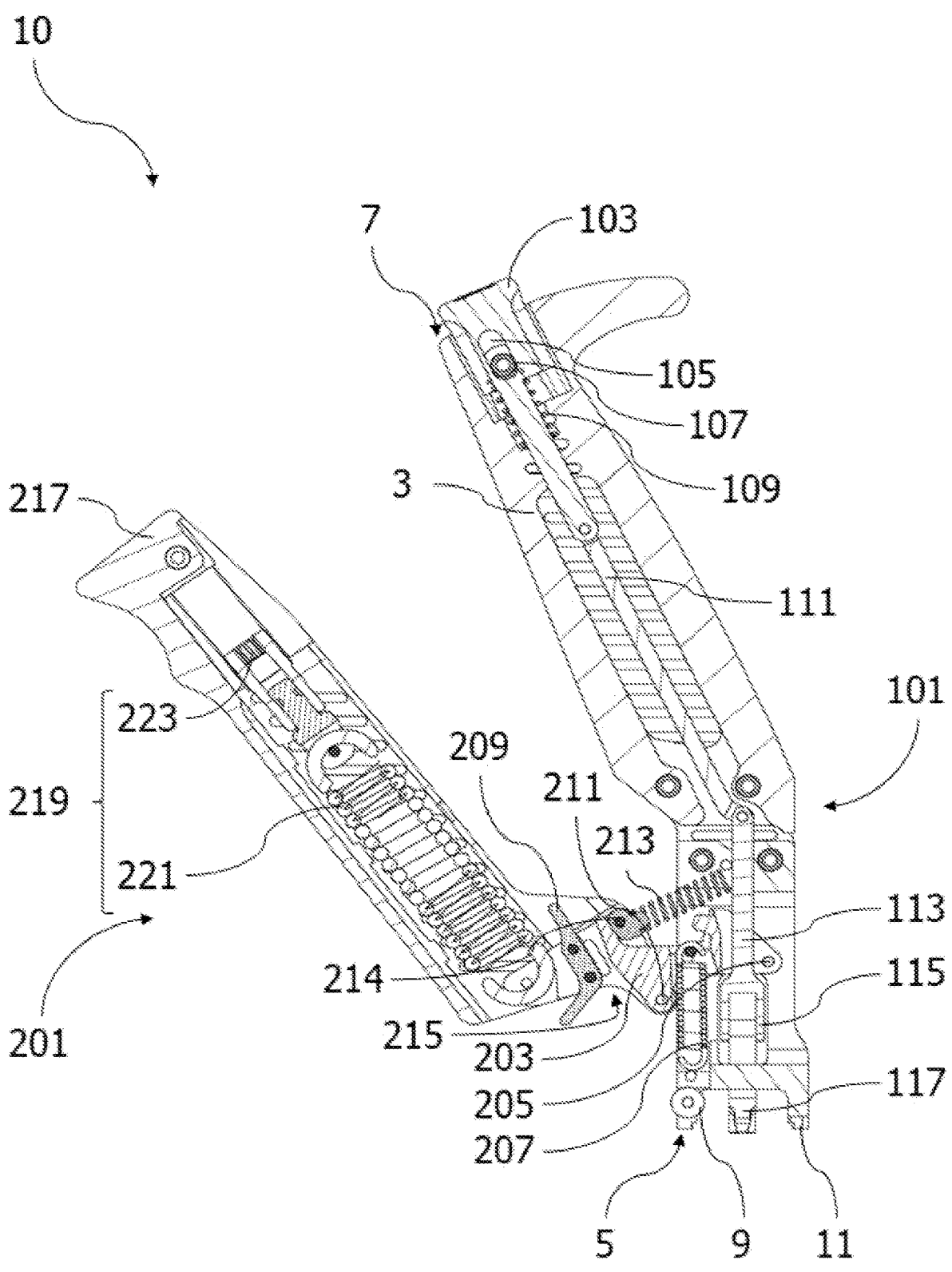
FIG. 13 is a lateral cross-section view of the alternative surgical tensioning instrument of FIG. 12 in the open position and the spring member in an initial position corresponding to the state shown in FIG. 1.

FIGS. 12 and 13 show an alternative surgical tensioning instrument 10, which differs from the previous in that, at or above the tension threshold, pivoting is not about the connecting axis 214 but about the connecting axis 211, since the actuator 217 has one end portion that is hinged to the grip 209 by means of the grip pivot axis 211 to pivot independently from the grip 209 and the traveler 203 about the grip pivot axis 211.

Clamping Process

Figure 4:
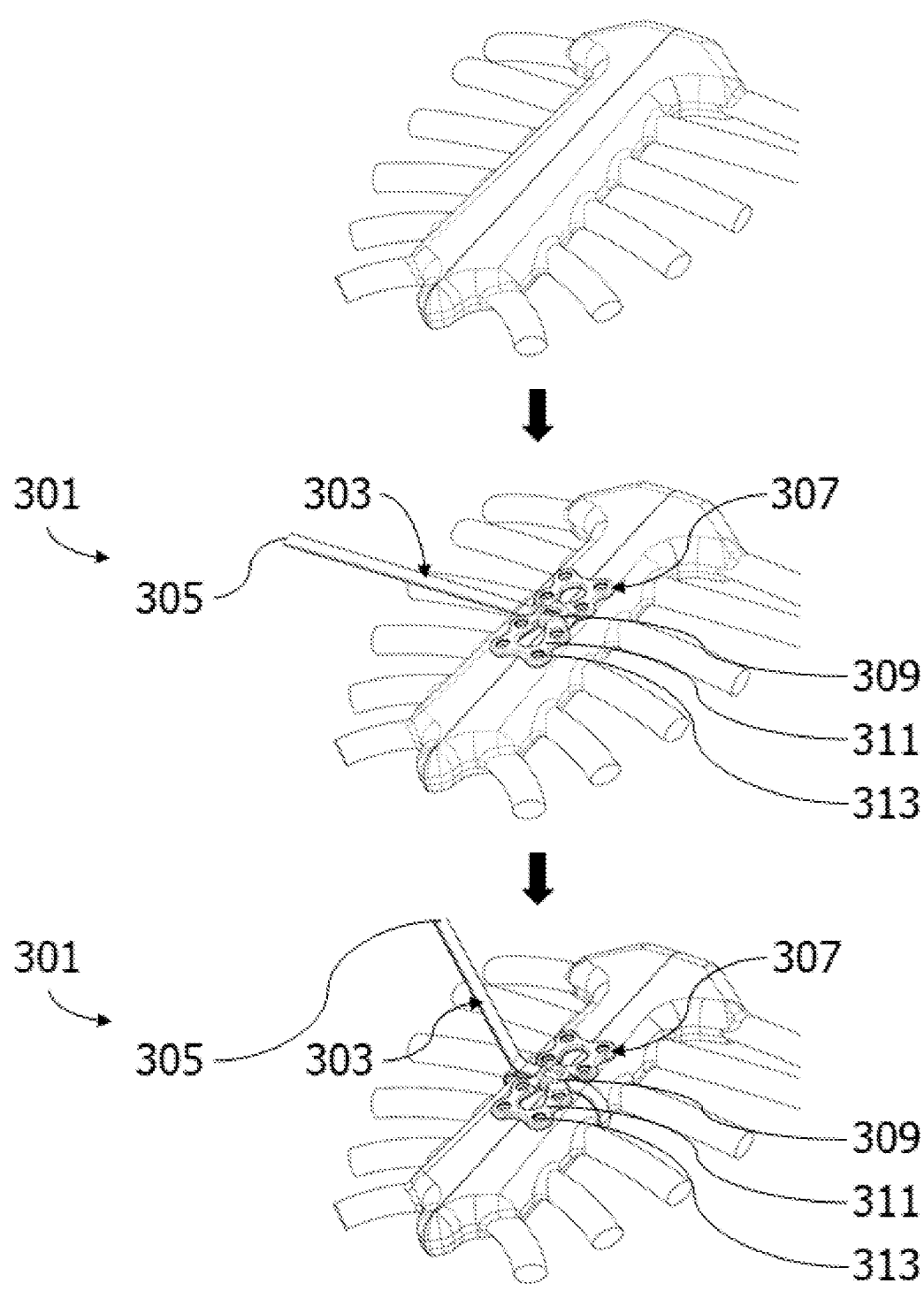
FIG. 4 is a perspective top view on two sternum halves that are to be secured to each other (top illustration) by placing a surgical tensioning member on top (middle illustration) and forming a tight loop about them by means of a strap portion of the surgical tensioning member cooperating with a locking portion of the surgical tensioning member (bottom illustration)

In the exemplary surgical scenario of FIG. 4, two sternum halves are to be secured together (top illustration; which of course does not limit usability of the surgical tensioning instrument 1). For this purpose, a surgical tensioning member 301 is placed on at least one of the two sternum halves (middle illustration). Then, a tight loop is formed about them by means of a strap portion 303 of the surgical tensioning member 301. For this purpose, the free end 305 of the strap portion 303 is pulled around the two sternum halves and passed through a locking portion 307 of the surgical tensioning member 301 (bottom illustration) in the manner of a conventional zip tie. The locking portion 307 comprises a locking head 309, which is configured to secure the strap portion 303 to the locking portion 307, and a locking plate 311, which provides engagement holes 313 for securing the locking plate 311 via fasteners, such as screws, to at least one of the two sternum halves. Of course, this process can be applied to any target bone or parts thereof, not just to the shown sternum halves.

In some variants, the locking plate 311 is made from metal (e.g., from titanium). In such or other variants, the strap portion 303 and the locking head 309 may form an integral (e.g., injection molded) polymeric component coupled to the locking plate 311. In still further variants, the entire member 301 is made as an injection molded component, with the engagement holes 313 optionally being defined by metallic, ring-shaped inserts.

Figure 5:
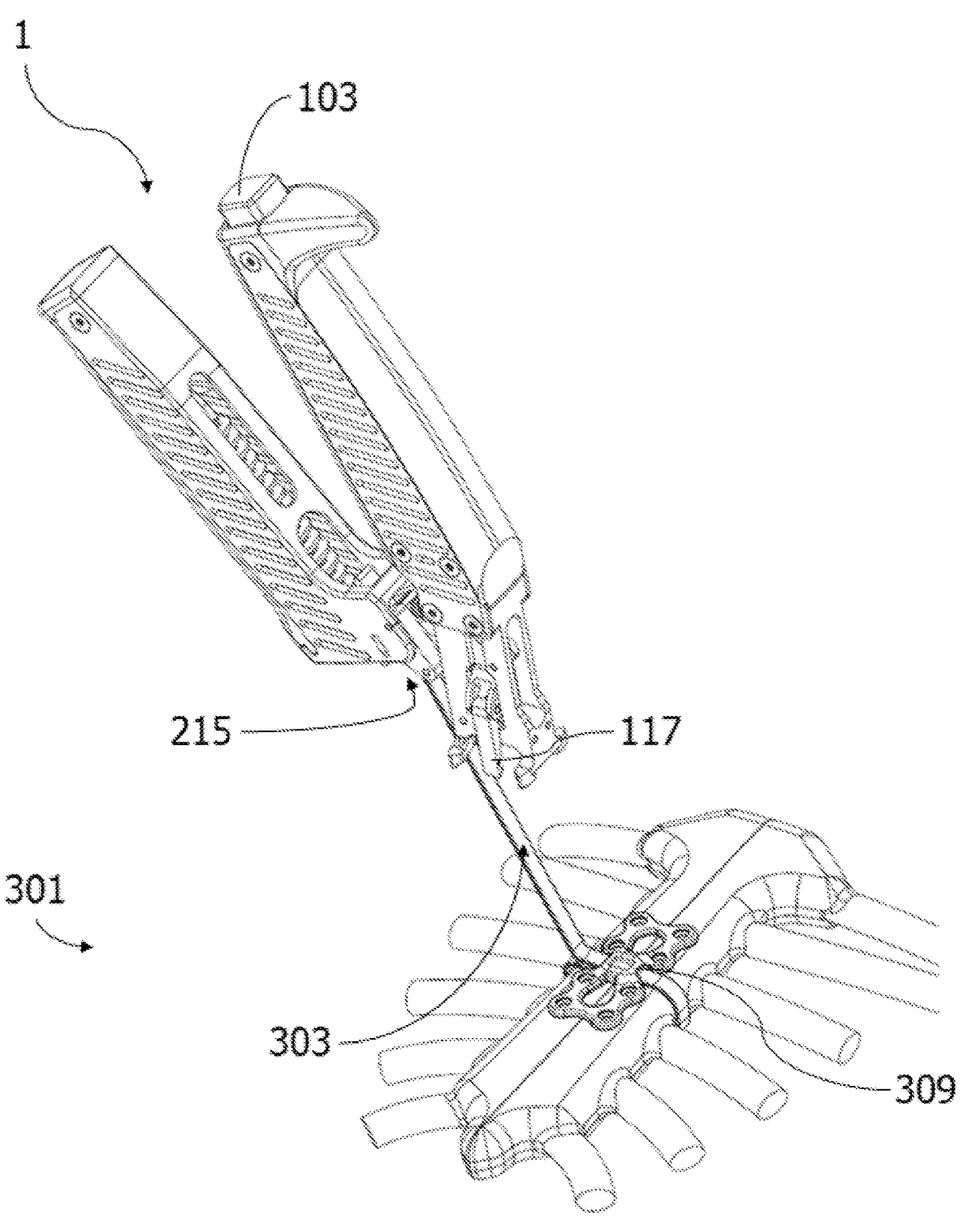
FIG. 5 is a perspective top view of the surgical tensioning instrument approaching the surgical tensioning member in FIG. 4 from the top and towards a free end of the strap portion, wherein the clamping jaws are still in the closed position.

In FIG. 5, the surgical tensioning instrument 1 is approaching the surgical tensioning member 301 from a direction towards the strap portion 303 protruding from the locking head 309. The surgical tensioning member 1 is in the initial state, where the button 103 is not being pushed and the clamping jaws 117 are in their closed position. The free end 305 (not visible) of the strap portion 303 is inserted into the grip channel 215, see FIG. 1.

Figure 6:
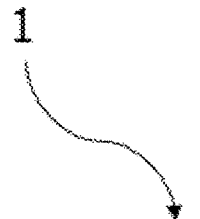
FIG. 6 is a perspective top view in accordance with FIG. 5, wherein the locking portion is in contact with an interface of the surgical tensioning instrument, wherein the free end of the strap portion is inserted into the surgical tensioning instrument and the clamping jaws are in the open position.

In FIG. 6, the surgical tensioning instrument 1 is contacting the locking portion 307 such that the interface 11 holds the locking portion 307 laterally to avoid lateral displacement of the front end 5 of the body 3 relative to the surgical tensioning member 301. Here, the button 103 is pushed and the clamping jaws 117 are open—as in FIG. 1 and FIG. 2. The free end 305 of the strap portion 303 has passed through and protrudes from the grip channel 215, wherein the grip channel 215 leads the strap portion 303 into a space between the actuator 217 and the body 3.

In FIG. 7, while pressing the front end 5 of the body 3 against the locking portion 307, the button 103 is released and the clamping jaws 117 are closed—as in FIG. 3—to lock on to the locking portion 307, in particular to the locking head 309. Now the surgical tensioning instrument 1 is fixedly attached to the surgical tensioning member 301 and cannot be pulled away from it. Instead of locking to the locking head 309, the locking may occur to the locking plate 311.

Tensioning Process

FIG. 8 shows a lateral view of the configuration and state shown in FIG. 7. This view will better illustrate the next steps in the process, since it better shows the further tensioning of the strap portion 303, which protrudes from the locking head 309, is guided by the pulley 9 towards the grip channel 215 and passes through the grip channel 215.

In FIG. 9, the actuator 217 is pulled in the direction of the shown clockwise direction indicated by a curved arrow towards the body 3 and pivots together with the grip 209 about the grip pivot axis 211 against the force of the grip spring 213. Thereby, the grip channel 215 is closed and the strap portion 303 is gripped between the grip 209 and the still stationary traveler 203.

Figure 10:
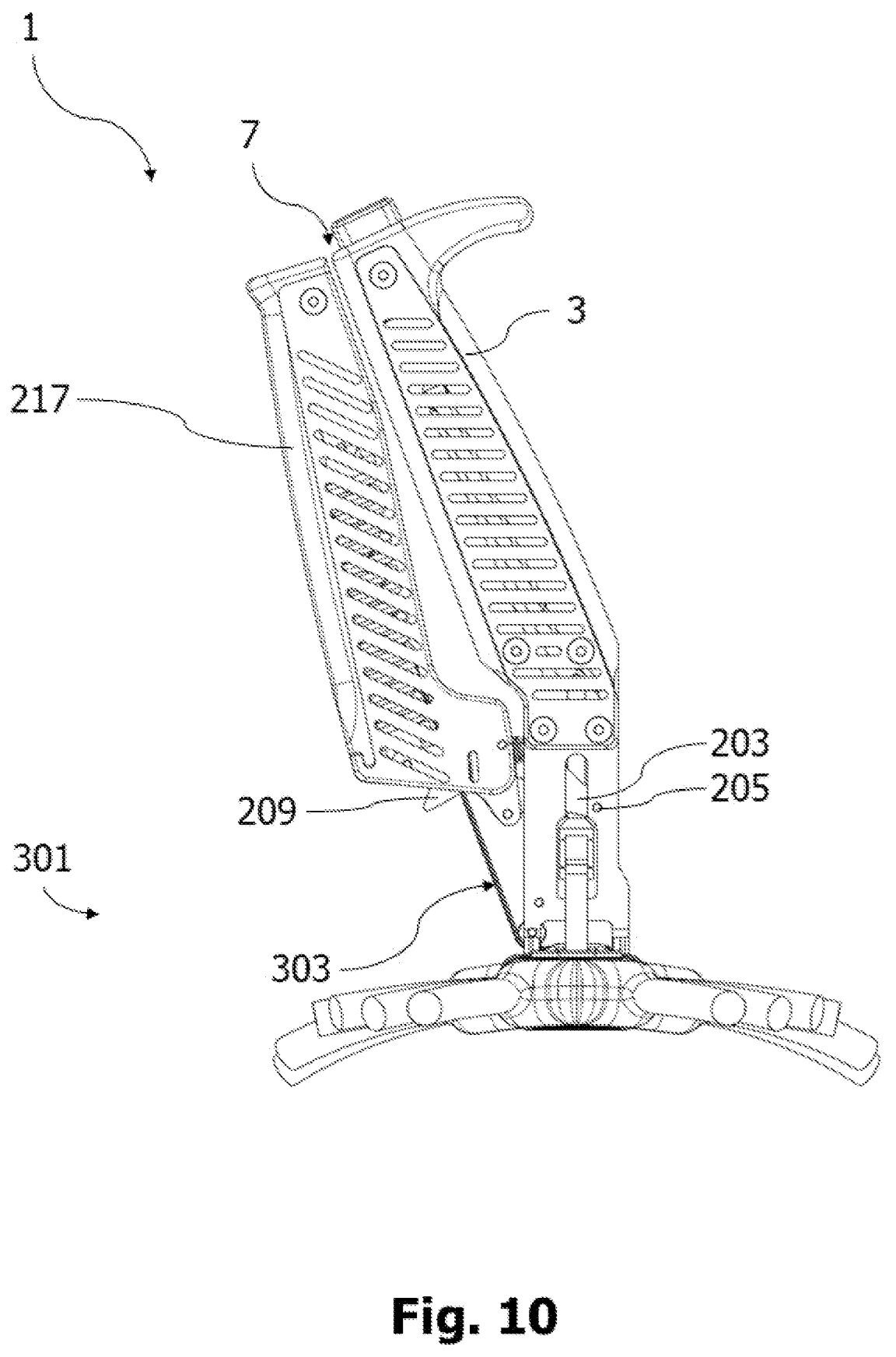

In FIG. 10, the actuator 217 is pulled further towards the body 3 with the strap portion 303 gripped. When the tension in the surgical tensioning member 301 looped about the sternum halves is less than a tension threshold, the actuator 217 pivots together with the grip 209 and the traveler 203 about the traveler pivot axis 205. Thereby, the strap portion 303 is pulled towards the back end 7 of the body 3 to further tension the surgical tensioning member 301 about the two sternum halves.

Figure 11:
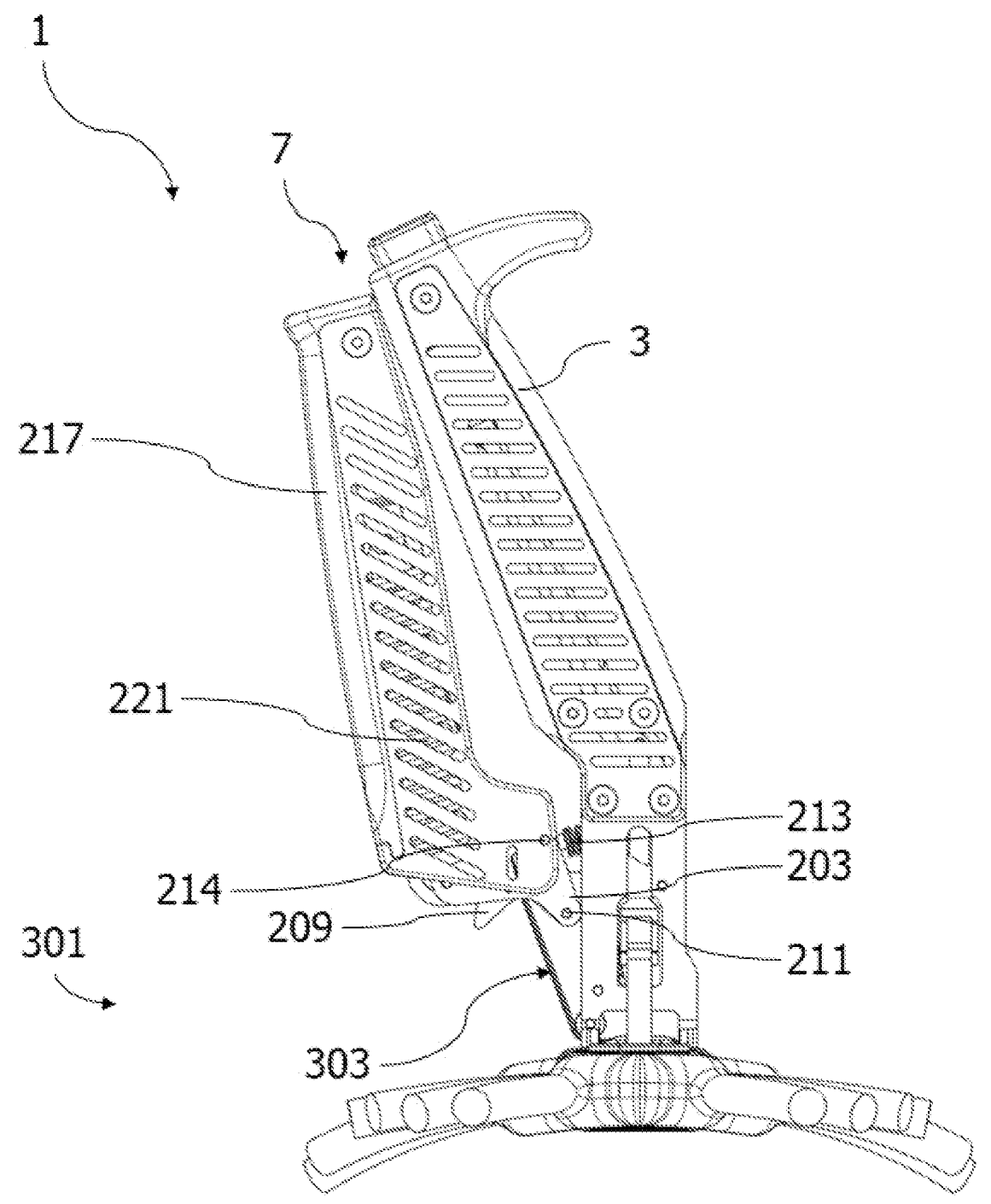
FIG. 11 is a lateral view in accordance with FIG. 9, wherein the actuator of the surgical tensioning instrument is further moved clockwise towards the body of the surgical tensioning instrument to maintain the tension in the surgical tensioning member about the two sternum halves, when the tension in the surgical tensioning member reaches or exceeds the tension threshold.

In FIG. 11, the actuator 217 is also pulled further towards the body 3 with the strap portion 303 gripped. When the tension in the surgical tensioning member 301 reaches or exceeds the tension threshold, the actuator 217 pivots about the connecting axis 214, while the grip 209 and the traveler 203 remain stationary, i.e. the grip 209 does not pivot further about the grip pivot axis 211 and the traveler does not pivot further about the traveler pivot axis 205. Instead, the tension limiter spring 221 is stretched. Thereby, the strap portion 303 is not pulled further towards the back end 7 of the body 3 and the tension of the surgical tensioning member 301 about the two sternum halves is not increased further.

In FIG. 12, which shows the alternative surgical tensioning instrument 10 in the same state as the previous surgical tensioning instrument 1 in FIG. 11, the actuator 217 pivots about the grip pivot axis 211, while the grip 209 and the traveler 203 remain stationary, i.e. the grip 209 does not pivot further about the grip pivot axis 211 and the traveler does not pivot further about the traveler pivot axis 205 shown in FIG. 13.

As has become apparent from the above description of an exemplary embodiment, the clamping mechanism 101 is easy, intuitive and reliable to use. After being fixedly attached to the surgical tensioning member 301, the surgical tensioning instrument 1 can easily be removed from the member 301 by actively opening the at least one clamping jaw 117. Thereby, undesired (e.g., pulling) forces on the surgical tensioning member 301 that may occur in an (uncontrollable) passive opening of the clamping jaws can be avoided. In some variants, the clamping mechanism 101 can be opened by an operator's hand while holding the surgical tensioning instrument 1 for tensioning of the surgical tensioning member 301, e.g., by the operator's thumb, in the exemplary embodiment, or any other finger of the tensioning hand already holding the surgical tensioning instrument 1. In some configurations, the clamping mechanism 101 further allows a force acting on the at least one movable clamping jaw 117 directly to close it, but prevents a force acting on the jaw 117 directly to open it. Thereby, an accidental opening of the at least one clamping jaw 117 can be prevented.

As has also become apparent from the above description of an exemplary embodiment, the tensioning mechanism 201 is easy, intuitive and reliable to use. The tension limiter spring 221 being configured to stretch longitudinally upon operation of the tensioning mechanism 201 may in some implementations at the same time compress in a direction orthogonal to its longitudinal extension. This means that the tension limiter spring 221 requires less space in a direction orthogonal to its longitudinal extension when the tensioning mechanism 201 is operated compared to when the tensioning mechanism 201 is not operated. Thereby, tension limiter spring 221 can be integrated in a slimmer actuator 217, for example, which already extends longitudinally a significant amount to be comfortable for an operator's hand, compared to a tension limiter spring that is compressed longitudinally upon operation of the tensioning mechanism. This ability of the tension limiter spring 221 to compress in a direction orthogonal to its longitudinal extension upon operation further allows the space between the actuator 217 and the body 3 to be increased, which can provide a larger range of motion for the tensioning operation, where the actuator 217 is moved in the first direction and towards the body 3. In case the tension limiter spring 221 breaks or is otherwise impaired, the operator would immediately notice its failure, since the actuator 217 could then be moved towards the body 3 without any resistance from the tension limiter spring 221, thereby rendering an uncontrolled tensioning of the surgical tensioning member 301 impossible. As such, operational safety can be increased.

Finally, the overall design of the surgical tensioning instrument 1 is optimized to be cost efficient and easily maintainable. This is in particular achieved by the use of common axes, for example the grip pivot axis 211, integrated components, for example the tension limiter 219 in the actuator 217 and/or the mechanical linkage in the body 3, and separation of mechanisms, for example the clamping mechanism 101 and the tensioning mechanism 201, which are operated and work independently, such that if one fails for whatever reason, the other remains functional.

LIST OF REFERENCE SIGNS

1, 10—Surgical tensioning instrument
3—Body
5—Front end
7—Back end
9—Pulley
11—Interface
101—Clamping mechanism
201—Tensioning mechanism
103—Button
105—Button through-hole
107—Button guide
109—Button spring
111—First rod
113—Second rod
115—Second rod through-hole
117—Clamping jaw
203—Traveler
205—Traveler pivot axis
207—Traveler spring
209—Grip
211—Grip pivot axis
213—Grip spring
214—Connecting axis
215—Grip channel
217—Actuator
219—Tension limiter
221—Tension limiter spring
223—Tension limiter adjustment mechanism
301—Surgical tensioning member
303—Strap portion
305—Free end

15

307—Locking portion
309—Locking head
311—Locking plate
313—Engagement holes
The invention claimed is:

1. A surgical tensioning instrument comprising:
a body defining a front end and an opposing rear end;
a grip movable relative to the body and configured to
secure a strap portion of a surgical tensioning member
to the surgical tensioning instrument;
an actuator operatively coupled to the body and config-
ured to move from an initial position toward a tension-
ing position in response to an applied force, causing the
grip to move in a tensioning direction; and
a clamping mechanism configured to secure a locking
portion of the surgical tensioning member to the sur-
gical tensioning instrument, wherein the clamping
mechanism includes opposed clamping jaws at the
front end of the body, at least one of the clamping jaws
being configured to be movable between a closed
position, in which the locking portion is secured to the
surgical tensioning instrument, and an open position, in
which the locking portion is released from the surgical
tensioning instrument;
wherein the clamping mechanism is operable to move the
at least one of the clamping jaws from the closed
position to the open position; and
wherein the front end of the body includes a front end
surface that faces the locking portion, and wherein the
clamping mechanism includes a release button protrud-
ing from a rear end surface of the body that is opposite
the front end surface of the body and configured to
move at least one of the clamping jaws from the closed
position to the open position.

2. The surgical tensioning instrument according to claim
1,
wherein the at least one movable clamping jaw is hinged
to the body and configured to pivot between the closed
position and the open position.

3. The surgical tensioning instrument according to claim
2,
wherein the at least one movable clamping jaw has a
central portion between two opposed end portions, and
wherein the central portion of the at least one movable
clamping jaw is hinged to the body.

4. The surgical tensioning instrument according to claim
1,
wherein the clamping mechanism comprises a mechanical
linkage of components configured to be movable in a
direction towards the front end or in a direction towards
the rear end of the body.

5. The surgical tensioning instrument according to claim
1,
wherein the at least one movable clamping jaw is con-
figured to cooperate with a rod, which is operable to
move the at least one movable clamping jaw from the
closed position to the open position.

6. The surgical tensioning instrument according to claim
5,
wherein the rod is configured to act as a push rod.

7. The surgical tensioning instrument according to claim
5,
wherein the clamping mechanism comprises a mechanical
linkage of components configured to be movable in a
direction towards the front end or in a direction towards
the rear end of the body, and wherein the rod forms part
of the mechanical linkage.

8. The surgical tensioning instrument according to claim
5,
wherein the button is configured to actuate the rod.

9. The surgical tensioning instrument according to claim
5,
wherein the button and the rod extend along different
longitudinal directions.

10. The surgical tensioning instrument according to claim
1,
wherein the clamping jaws protrude laterally from the
body.

11. The surgical tensioning instrument according to claim
1,
wherein the clamping mechanism is biased such that the
closed position is held when the clamping mechanism
is not operated.

12. The surgical tensioning instrument according to claim
1,
wherein the clamping mechanism is configured to actively
move the opposed clamping jaws from the closed
position to the open position.

13. A surgical tensioning instrument comprising:
a body defining a front end and an opposing rear end;
a grip movable relative to the body and configured to
secure a strap portion of a surgical tensioning member
to the surgical tensioning instrument;
an actuator operatively coupled to the body and config-
ured to move from an initial position toward a tension-
ing position in response to an applied force, causing the
grip to move in a tensioning direction; and
a clamping mechanism configured to secure a locking
portion of the surgical tensioning member to the sur-
gical tensioning instrument, wherein the clamping
mechanism comprises opposed clamping jaws at the
front end of the body, at least one of the clamping jaws
being configured to be movable between a closed
position, in which the locking portion is secured to the
surgical tensioning instrument, and an open position, in
which the locking portion is released from the surgical
tensioning instrument;
wherein the clamping mechanism is operable to move the
at least one of the clamping jaws from the closed
position to the open position;
wherein the at least one movable clamping jaw is con-
figured to cooperate with a rod, which is operable to
move the at least one movable clamping jaw from the
closed position to the open position; and
wherein the rod at least partially extends through the body
and is only permitted to move translationally relative to
the body.

14. The surgical tensioning instrument according to claim
13,
wherein the rod is surrounded by the body.

15. The surgical tensioning instrument according to claim
13,
wherein the rod is completely disposed within the body.

16. A surgical tensioning system comprising:
a surgical tensioning member including a locking portion
and a strap portion integrally formed;
a surgical tensioning instrument comprising:
a body defining a front end and an opposing rear end;
a grip movable relative to the body and configured to
secure the strap portion of the surgical tensioning
member to the surgical tensioning instrument;
an actuator operatively coupled to the body and con-
figured to move from an initial position toward a tensioning position in response to an applied force, causing the grip to move in a tensioning direction; and a clamping mechanism configured to secure the locking portion of the surgical tensioning member to the surgical tensioning instrument, wherein the clamping mechanism comprises opposed clamping jaws at the front end of the body, at least one of the clamping jaws being configured to be movable between a closed position, in which the locking portion is secured to the surgical tensioning instrument, and an open position, in which the locking portion is released from the surgical tensioning instrument;

wherein the clamping mechanism is operable to move the at least one of the clamping jaws from the closed position to the open position;

wherein the at least one clamping jaw is configured to engage the locking portion of the surgical tensioning member in the closed position; and wherein the locking portion includes a locking plate and a locking head, wherein the locking plate is configured to attach to bone and the locking head is configured to engage the strap portion, and wherein the at least one clamping jaw is configured to engage at least a portion of the locking plate in the closed position.

17. The surgical tensioning system according to claim 16, wherein the strap portion is configured to be pulled through the locking portion along a first direction so as to form a loop about a target bone and the locking portion is configured to prevent the strap portion from moving along a second direction opposite the first direction, and wherein the strap portion defines a free end that extends out of the locking portion.

18. The surgical tensioning system according to claim 16, wherein the locking plate and locking head are formed from different materials.

19. The surgical tensioning system according to claim 16, wherein the locking plate is formed from metal and the locking head is formed from a polymeric material.

20. The surgical tensioning system according to claim 16, wherein engagement of the locking plate of the locking portion of the surgical tensioning member by the at least one movable clamping jaw and another opposite movable or immovable clamping jaw causes the body of the surgical tensioning instrument to be fixedly attached to the locking plate of the locking portion of the surgical tensioning member.

* * * * *